United States Patent [19]

Schlosser et al.

[11] Patent Number: 5,207,654
[45] Date of Patent: May 4, 1993

[54] STORAGE DEVICE WITH POSITIVE DISPLACEMENT DISPENSER BY MEANS OF EGRESS THROUGH A PIERCED SEPTUM

[75] Inventors: Mark S. Schlosser, Seattle, Wash.; Lionel S. Goldring, Irvine, Calif.

[73] Assignee: SpaceLabs Medical, Inc., Redmond, Wash.

[21] Appl. No.: 535,903

[22] Filed: Jun. 11, 1990

[51] Int. Cl.⁵ ............................................. A61B 5/00
[52] U.S. Cl. ................................. 604/203; 604/200; 604/201; 604/218; 604/231
[58] Field of Search ............... 604/203, 38, 143, 194, 604/36, 164, 233, 403, 218, 231, 236, 200, 201

[56] References Cited

U.S. PATENT DOCUMENTS

| | | | |
|---|---|---|---|
| 3,534,735 | 10/1970 | Sly | 604/231 |
| 4,020,831 | 5/1977 | Adler | 604/231 X |
| 4,037,464 | 7/1977 | Wenander | 604/231 |
| 4,191,225 | 3/1980 | Ogle | 604/231 X |
| 4,259,956 | 4/1981 | Ogle | 604/231 X |
| 4,390,016 | 6/1983 | Riess | 604/194 X |
| 4,648,532 | 3/1987 | Green | 604/200 X |
| 4,684,366 | 8/1987 | Denny et al. | 604/130 |
| 4,828,540 | 5/1989 | Walter | 604/164 |
| 4,976,966 | 12/1990 | Theeuwes et al. | 604/892.1 |
| 4,982,740 | 1/1991 | Broden | 604/415 X |

Primary Examiner—Robert A. Hafer
Assistant Examiner—Kerry Owens
Attorney, Agent, or Firm—Seed and Berry

[57] ABSTRACT

A positive displacement ampule for storing a fluid therein and dispensing the fluid therefrom. The ampule includes an elongate vessel for storing the fluid having a large diameter base portion at one end thereof joined to a small diameter stem portion at the other end thereof, a piston disposed in the vessel at the base end thereof for forcing the fluid from the vessel, a fracture probe for fracturing the base end of the vessel and a needle for inserting into the fractured base end of the vessel and for piercing the piston such that one end of the needle protrudes outwardly from the vessel and the other end of the needle communicates with the fluid in the vessel. In this manner, the fluid is pumped from the vessel through the needle by pushing the piston in the direction of the fluid. The positive displacement ampule is manufactured by providing the elongate vessel with the stem end of the vessel being open and the base end of the vessel being closed, injecting a monomer liquid into the vessel through the open stem end thereof, polymerizing the liquid so as to convert the liquid to a solid designed to function as a piston, injecting the fluid into the vessel through the open stem end thereof in such a manner as to maintain the fluid between the piston and the stem end and sealing the stem end of the vessel.

34 Claims, 2 Drawing Sheets

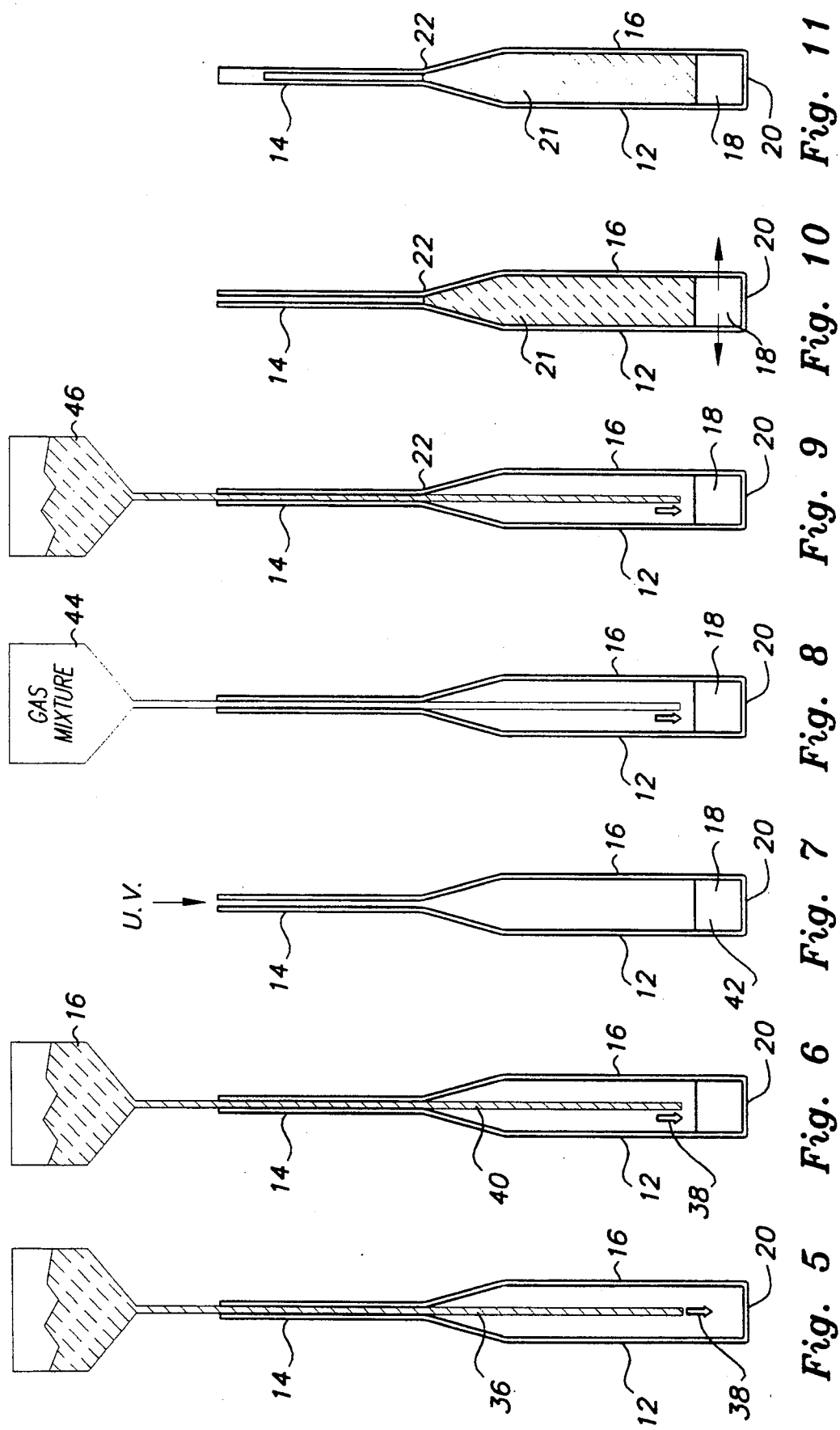

STORAGE DEVICE WITH POSITIVE DISPLACEMENT DISPENSER BY MEANS OF EGRESS THROUGH A PIERCED SEPTUM

TECHNICAL FIELD

This invention relates to a storage device, and more particularly, to a storage device having a positive displacement dispenser for dispensing fluid therefrom.

BACKGROUND OF THE INVENTION

There are three types of ampules that are presently known: a pressurized ampule, an evacuated ampule and a non-pressurized ampule. The pressurized ampule contains fluid or powder which is at a pressure greater than atmospheric pressure such that the fluid or powder is propelled from the ampule by breaking the tip of the ampule. This type of ampule is manufactured by introducing the fluid or powder into the opened tip end of the ampule in a pressurized atmosphere and thereafter sealing the ampule.

The evacuated ampule is primarily designed for conducting chemical analyses of water. The evacuated ampule contains a fluid at a pressure that is less than atmospheric pressure. The analysis is conducted by breaking the tip of the ampule while immersed in the water being analyzed. Due to the low pressure in the ampule relative to the environment, the water is forced into the ampule and mixes with the analyzing fluid or powder. The water is analyzed by observing the change in color of the mixed fluid.

The non-pressurized ampule includes stem portions at opposite ends and is filled with a fluid, such as a medicine, at atmospheric pressure. To dispense the fluid, both stems are broken and the fluid is drained from the ampule.

There are no known ampules having positive displacement capabilities which permit the user to pump the fluid contained in the ampule therefrom. Further, there are no known positive displacement devices which store fluids with gases trapped in predictable volume regions.

SUMMARY OF THE INVENTION

The present invention resides in a positive displacement ampule which allows the user to pump the fluid therefrom. The positive displacement ampule comprises an elongate vessel for storing a fluid therein having a large diameter base portion at one end thereof joined to a small diameter stem portion at the other end thereof, a piston disposed in the vessel at the base end thereof for forcing the fluid from the vessel, a fracture probe for fracturing the base end of the vessel and a needle for inserting into the fractured base end of the vessel and for piercing the piston such that one end of the needle protrudes outwardly from the vessel and the other end of the needle communicates with the fluid. In this manner the fluid is pumped from the vessel through the needle by pushing the piston in the direction of the fluid. The base of the vessel has a weakened area which permits the fracturing thereof by conventional means.

The positive displacement ampule is manufactured by manufacturing the elongate vessel with the stem end of the vessel being open and the base end of the vessel being closed, injecting a monomer liquid into the vessel through the open stem end thereof, polymerizing the liquid so as to convert the liquid to a solid, the solid being designed to function as a piston, injecting the fluid into the vessel through the open stem end thereof in such a manner as to maintain the fluid between the piston and the stem and sealing the stem end of the vessel.

BRIEF DESCRIPTION OF THE DRAWINGS

FIGS. 5 through 11 are elevational views showing the method of manufacturing the ampule according to the present invention.

DETAILED DESCRIPTION OF THE INVENTION

Figure 1:
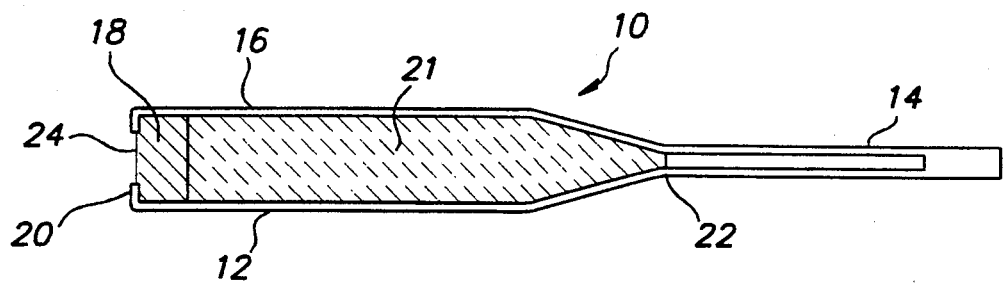
FIG. 1 is an elevational view of the positive displacement ampule according to the present invention.

Referring to FIG. 1, the positive displacement ampule 10 is an elongate vessel 12 having a small diameter stem 14 at one end thereof joined to a relatively large diameter portion 16 at the other end thereof. A cylindrical piston 18 is disposed at the base 20 of the large diameter portion with fluid 21 being contained between the piston 18 and the bottom 22 of the stem 14.

Figure 2:
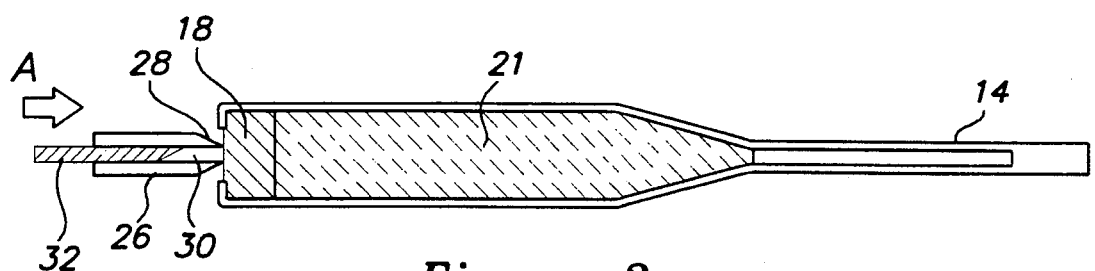
FIGS. 2 through 4 are elevational views showing the method by which the fluid in the ampule is withdrawn therefrom.

The base 20 has a weakened area 24 at the central portion thereof such that the user can fracture that portion of the base with a probe 26 illustrated in FIG. 2. The weakened area 24 can be formed by, for instance, reducing the thickness of the base of the vessel, scoring a circle in the base or providing a ceramic piece in the base. According to the preferred embodiment of the invention, the vessel 12 is made of glass and the base 20 has a plastic coating adhered to the exterior thereof. In this manner, when the base 20 is fractured the glass shards shards are retained by the coating. As illustrated in FIG. 2, the probe 26 has a pointed end 28 for fracturing the base 20 and has a bore 30 extending axially therethrough for slidably receiving a needle 32.

Figure 3:
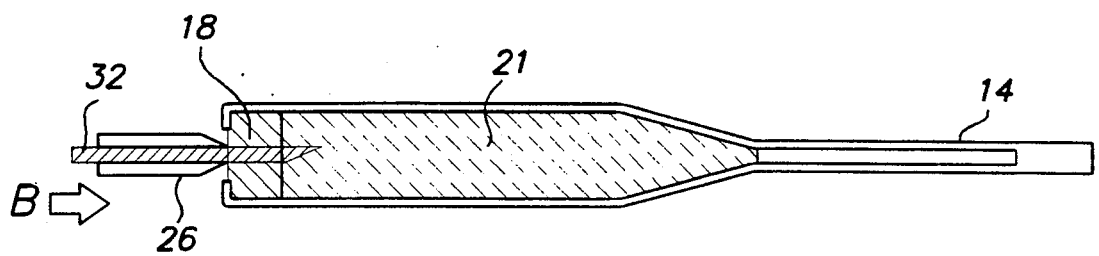
Figure 4:
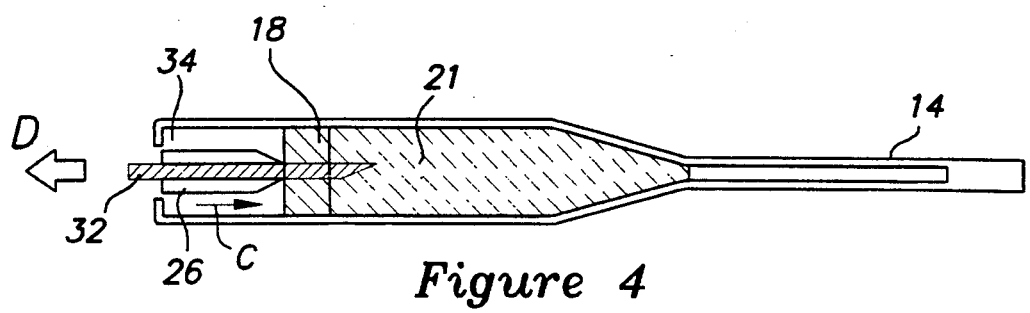

FIGS. 2 through 4 illustrate the manner in which the fluid 21 is withdrawn from the vessel 12. Referring to FIG. 2, as noted above, the base 20 of the vessel 12 is fractured by pushing the probe 26 in the direction of arrow A against the base with the necessary force. Since the base is coated with plastic, the glass shards resulting from the fracturing of the base are retained by the base. After the base 20 has been fractured, the needle 32 is pushed in the direction of arrow B illustrated in FIG. 3 to thereby pierce the piston 18 such that the needle extends into the interior of the vessel so as to communicate with the fluid 21. Thereafter, as shown in FIG. 4, both the probe 26 and the needle 32 are moved in the direction of arrow C causing the fluid to pumped through the needle and ejected from the vessel as illustrated by arrow D. The glass shards are forced into the area 34 disposed between the base 20 of the vessel 12 and the piston 18 such that they do not contaminate the ejected fluid.

Accordingly, as can be seen from the foregoing, the fluid in the vessel can be withdrawn without the necessity of fracturing the vessel in two places as in the conventional ampule discussed above. Rather, only one end of the vessel need be fractured.

FIGS. 5 through 11 illustrate the method by which the ampule 10 is manufactured. Referring to FIG. 5, initially, the vessel 12 is open at the top of the stem 14 and closed at the base 20 of the large diameter portion 16. A needle 36 is inserted into the opening and a coating agent 38 applied to the interior of the base 20. The coating agent is designed to insure that the piston liquid that is subsequently injected and polymerized does not stick to the interior of the vessel 12. After coating the base, another needle 40 is inserted through the opening and a monomer 42 containing a polymerizing agent in the form of a liquid is injected into the vessel as shown in FIG. 6. An important characteristic of the polymerizeable monomer is that, once polymerized, it expands when exposed to an aqueous solution (i.e., it is water-swellable). The specific monomer utilized is in the HEMA family and has the chemical name POLYHYDROXYETHYLMETHACRYLATE. An example of a polymerizing agent is BENZOYL PEROXIDE (which is polymerized by heat) or 2,2,DIETHOXY ACETOPHENONE (which is polymerized by ultraviolet light).

As illustrated in FIG. 7, the monomer liquid 42 is polymerized by exposing the liquid to ultraviolet light or, alternatively, to heat. By polymerizing the liquid, the cylindrical piston 18 is formed which is utilized to force the fluid in the vessel therefrom, as described above.

If it is important to maintain the gas concentration of the fluid in the vessel after the fluid has been polymerized, the vessel 12 may be filled with a tonometered gas mixture 44 and, thereafter, a tonometered calibrant fluid 46, as illustrated in FIGS. 8 and 9, respectively. The calibrant fluid 46 contains a known amount of carbon dioxide, oxygen and nitrogen in terms of partial pressure. This is important because when analyzing the oxygen and carbon dioxide content of blood a flow cell must be calibrated by passing a calibrant fluid having a known amount of carbon dioxide and oxygen into the flow cell. In order to prevent the calibrant fluid from releasing any of its gases and to thereby maintain the proper ratio of gases in the calibrant fluid when injecting the fluid into the vessel, it is recommended that the vessel be filled with a gas mixture having the same percentage of gases as the calibrant fluid. Accordingly, as noted above, a gas mixture 44 having a known percentage of gases, which are correspondingly present in the calibrant fluid 46, is injected into the vessel 12 prior to the injection of the calibrant fluid 46.

Subsequent thereto, as noted above, the calibrant fluid 46 is injected utilizing a needle, as illustrated in FIG. 9, such that the fluid extends up to the bottom 22 of the stem 14. At this time, the piston 18 swells sufficiently to press firmly against the interior wall of the vessel to thereby provide an adequate piston seal, as shown in FIG. 10. Specifically, the piston seals the fluid 21 in the vessel 12 such that when the weakened central area 24 of the base 20 is fractured the fluid 21 does not leak past the piston 18 and from the vessel 12. After the fluid has been injected into the vessel, the top of the stem 14 is sealed, as shown in FIG. 11.

While the above description describes the manner in which a monomer liquid is injected into the vessel and thereafter polymerized to form the piston, it is of course understood that the invention is not intended to be limited to this embodiment. Rather, any liquid (i.e., any viscous substance) that can be converted to a solid may be used to form the piston. For instance, an epoxy liquid could be injected into the vessel and thereafter converted to a solid by curing it. Moreover, while the above embodiment is directed towards filling the vessel with a calibrant fluid, it should be understood that any appropriate fluid could be stored in the vessel, such as a wash fluid. Thus, the step of injecting a tonometered gas mixture is not always required.

The vessel is capable of being filled to greater than 90% of its volume. Moreover, the stem design insures that all of the gases in the vessel are trapped in the stem 14 of the vessel, and therefore, do not mix with the fluid. In particular, the inner diameter of the stem is designed to be less than 1 mm such that the stems act as a capillary tube. In this manner, the surface tension of the fluid acts to prevent the fluid from mixing with the gases. Thus, according to the invention, the fluid can be pumped from the ampule with the ampule disposed in any orientation without effecting the position of the gases in the vessel, as discussed above. Moreover, the pump arrangement allows the fluid to be pumped from the ampule at a specific rate. Of course, it is understood that the vessel 12 need not include the stem 14 if it is not important to prevent the mixing of the fluid and the gases.

When the fluid is withdrawn from the vessel in the manner described above, an air bubble forms at the leading edge of the flow to thereby form a negative fluid meniscus. The leading edge of the negative fluid meniscus serves to scrape previous fluids from the walls of the path, such as in a flow cell, so as to prevent the previous fluids from mixing with the present fluid thereby preventing what is commonly referred to as "carry-over".

The vessel can be made out of a gas impermeable material such as glass so as to insure that the gases in the fluid do not permeate the vessel. Alternatively, the vessel can be made out of gas permeable material such as plastic if maintaining the gas concentration in the fluid is not important.

We claim:

1. A positive displacement ampule, comprising:
an elongate vessel storing a fluid therein;
piston means disposed in one end of said vessel for forcing said fluid from said vessel, said fluid being disposed between said piston means and the other end of said vessel;
fracture means for fracturing said one end of said vessel; and
a needle insertable in said one end of said vessel in the area where said vessel has been fractured, said needle piercing said piston means such that one end of said needle protrudes outwardly from said vessel and the other end of said needle communicates with said fluid, wherein when said piston means is moved in the direction of said other end, said fluid is pumped from said vessel through said needle.

2. The ampule of claim 1 wherein said fracture means is a probe having a needle receiving bore disposed therein, and wherein said needle is slidably disposed in said bore.

3. The ampule of claim 2 wherein said probe is pointed at one end thereof for fracturing said vessel.

4. The ampule of claim 1 wherein said piston means is a waterswellable polymer which expands when saturated with a fluid so as to function as a piston.

5. The ampule of claim 4 wherein said vessel is cylindrical in shape and wherein said polymer is initially smaller than an inside diameter of said vessel such that when said polymer is saturated with fluid, said polymer expands so as to press against the inside circumference of said vessel.

6. The ampule of claim 1 wherein said one end of said vessel has a weakened area for permitting fracturing thereof.

7. The ampule of claim 6 wherein said weakened portion comprises one of a ceramic portion, a scored portion, and a reduced thickness portion.

8. The ampule of claim 1 wherein said one end is a large diameter base portion and said other end is a small diameter stem portion, said base portion being joined to said stem portion.

9. The ampule of claim 8 wherein the inside diameter of said stem portion is less than 1 mm.

10. A method of removing fluid from an ampule, said ampule including an elongate vessel for storing fluid therein, a piston disposed in said vessel at one end thereof and fluid disposed in said vessel between said piston and the other end of said vessel, said method comprising the following steps:
fracturing said one end of said vessel with a probe;
inserting a needle into said one end of said vessel in the area where said vessel has been fractured so as to pierce said piston such that one end of said needle protrudes from said vessel and the other end of said needle communicates with said fluid; and
pushing said piston towards said other end of said vessel so as to pump said fluid from said vessel through said needle.

11. The method of claim 11 wherein said inserting step comprises inserting said needle through a bore provided in said probe.

12. A method of manufacturing a positive displacement ampule, comprising the following steps:
manufacturing an elongate vessel, one end of said vessel being open, the other end of said vessel being closed;
injecting a liquid into said vessel through said open end thereof, said liquid being convertible to a solid;
converting said liquid to a solid, said solid being designed to function as a piston;
injecting a fluid into said vessel through said open end thereof in such a manner as to maintain said fluid between said piston and said open end;
sealing said open end of said vessel;
providing a fracture probe for fracturing said closed end of said vessel; and
providing a needle for inserting into said closed end after fracturing thereof and for piercing said piston such that one end of said needle protrudes outwardly from said vessel and the other end of said needle communicates with said fluid.

13. The method of claim 12 wherein said injecting step comprises injecting a polymerizeable fluid into said vessel.

14. The method of claim 13 wherein said converting step comprises polymerizing said polymerizeable fluid.

15. The method of claim 12, further comprising the step of providing a weakened area on said closed end such that said weakened area can be punctured.

16. The method of claim 15 wherein said step of providing a weakened area comprises manufacturing said closed end such that the thickness thereof is smaller than the thickness of the other walls of said vessel.

17. The method of claim 12 wherein said vessel is gas impermeable and said fluid is a tonometered calibrant.

18. The method of claim 17, further comprising the step of injecting a tonometered gas mixture into said vessel prior to injecting said tonometered calibrant, the same percentage of gases in said gas mixture being present in said calibrant.

19. The method of claim 12 wherein said manufacturing step comprises manufacturing said vessel such that said closed end has a larger diameter than said open end, the inside diameter of said open end being less than 1 mm.

20. An ampule system, comprising:
a vessel storing a fluid therein;
sealing means disposed in said vessel;
fracture means for fracturing a wall of said vessel in a predetermined area thereof;
a fluid contained in said vessel, said fluid being separated from said predetermined area by said sealing means;
a needle insertable through said predetermined area of said vessel after the wall of said vessel has been fractured, said needle then piercing said sealing means such that one end of said needle communicates with said fluid and the other end of said needle protrudes outwardly from said vessel; and
means for causing said fluid to flow from said vessel through said needle.

21. The ampule system of claim 20 wherein said sealing means is a piston slideably mounted in said vessel through which said needle extends when said needle has pierced said sealing means.

22. The ampule system of claim 21 wherein said means for causing said fluid to flow through said needle includes and actuator for forcing said piston into said vessel thereby displacing fluid from said vessel through said needle.

23. The ampule system of claim 20 wherein said vessel is an elongated container having a sidewall and at least one end wall, and wherein said predetermined area is in said end wall of said container.

24. The ampule system of claim 20 wherein said vessel is fabricated from glass, and wherein said end wall of said vessel is made relatively weak in said predetermined area thereby better allowing said fracture means to fracture said vessel in said predetermined area.

25. The ampule system of claim 20 wherein said fracture means is a probe having a needle receiving bore disposed therein, and wherein said needle is slideably disposed in said bore so that said probe may be used to fracture said vessel in said predetermined area thereby allowing said needle to puncture said sealing means through said fractured predetermined area of said vessel.

26. The ampule system of claim 20 wherein said fluid is a liquid.

27. A method of removing fluid from an ampule, said ampule including a vessel for storing fluid therein, a fluid disposed in said vessel, and a seal disposed in said vessel between said fluid and a predetermined area of a wall of said vessel, said method comprising:
fracturing said predetermined area of said wall of said vessel;
inserting a needle into said vessel through said predetermined area of said wall after said wall has been fractured so as to pierce said seal such that one end of said needle communicates with said fluid and the other end of said needle is externally accessible through said predetermined area of said wall; and
causing said fluid to flow from said vessel through said needle.

28. The method of claim 27 wherein said seal is a piston slideably disposed in said vessel, and wherein said step of causing said fluid to flow through said needle is accomplished by forcing said piston into said vessel thereby displacing said fluid from said vessel through said needle.

29. The method of claim 27 wherein said seal is a piston, and wherein said inserting and fracture steps are accomplished by:

providing an elongated probe having an axial bore, and a needle slideably mounted in said bore;

advancing said probe through said predetermined area of said wall of said vessel thereby fracturing said predetermined area;

advancing said needle relative to said probe thereby causing said needle to pierce said seal; and further advancing said probe and needle into said vessel so that said probe forces said piston into said vessel thereby displacing said fluid from said vessel.

30. A method of manufacturing an ampule, comprising:

manufacturing a vessel, one end of said vessel being open, the other end of said vessel being closed;

injecting a liquid into said vessel through said open end thereof, said liquid being convertible to a solid;

converting said liquid to a solid, said solid being designed to function as a seal;

injecting a fluid into said vessel through said open end thereof in such a manner as to maintain said fluid between said seal and said open end; and sealing said open end of said vessel.

31. The method of claim 30 wherein said injecting step comprises injecting a polymerizeable fluid into said vessel.

32. The method of claim 31 wherein said converting step comprises polymerizing said polymerizeable fluid.

33. The method of claim 30 wherein said vessel is gas impermeable and said fluid is a tonometered calibrant.

34. The method of claim 33, further comprising the step of injecting a tonometered gas mixture into said vessel prior to injecting said tonometered calibrant, the same percentage of gases in said gas mixture being present in said calibrant.

* * * * *